(12) United States Patent
Tyvoll et al.

(10) Patent No.: US 7,384,791 B2
(45) Date of Patent: Jun. 10, 2008

(54) METHOD OF ANALYZING BLOOD

(75) Inventors: David Tyvoll, La Jolla, CA (US); Winthrop D. Childers, San Diego, CA (US); Kirk Norton, San Diego, CA (US); Bryan J. Johnson, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 921 days.

(21) Appl. No.: 10/761,535

(22) Filed: Jan. 21, 2004

(65) Prior Publication Data

US 2005/0158704 A1 Jul. 21, 2005

(51) Int. Cl.
*G01N 33/48* (2006.01)
*G01N 27/00* (2006.01)
*G01N 1/18* (2006.01)

(52) U.S. Cl. .................. 436/95; 436/63; 436/149; 436/150; 436/164; 436/174; 436/175; 436/177; 422/82.01; 422/82.05; 422/101; 435/14; 204/547; 204/554; 204/556; 204/403.01; 204/643

(58) Field of Classification Search .................. 436/63, 436/95, 149, 150, 164, 174, 175, 177; 422/68.1, 422/82.01, 82.02, 82.05, 101; 435/4, 14; 204/547, 554, 556, 400, 403.01, 403.04, 204/643
See application file for complete search history.

(56) References Cited

U.S. PATENT DOCUMENTS

| | | | |
|---|---|---|---|
| 4,874,507 A | 10/1989 | Whitlock | |
| 4,911,806 A | 3/1990 | Hofmann | |
| 5,126,022 A | 6/1992 | Soane et al. | |
| 5,344,535 A | 9/1994 | Betts et al. | |
| 5,454,472 A | 10/1995 | Benecke et al. | |
| 5,626,734 A | 5/1997 | Docoslis et al. | |
| 5,653,859 A | 8/1997 | Parton et al. | |
| 5,658,444 A * | 8/1997 | Black et al. | 204/403.09 |
| 5,814,200 A | 9/1998 | Pethig et al. | |
| 5,858,192 A | 1/1999 | Becker et al. | |
| 5,938,904 A | 8/1999 | Bader et al. | |
| 5,993,630 A | 11/1999 | Becker et al. | |
| 5,993,631 A | 11/1999 | Parton et al. | |
| 6,056,861 A | 5/2000 | Fuhr et al. | |
| 6,059,950 A | 5/2000 | Dames et al. | |
| 6,149,789 A | 11/2000 | Benecke et al. | |

(Continued)

FOREIGN PATENT DOCUMENTS

EP 1 267 166 12/2002

(Continued)

OTHER PUBLICATIONS

Swiss Center for Electronics and Microtechnology, "Dielectrophoretic Size-Sensitive Particle Filter for MIcro-Fluidic Applications", 2 pgs., printed Feb. 24, 2004 from www.csem.ch. corporate/Report 2002/pdf/microrobotics.pdf.

(Continued)

*Primary Examiner*—Maureen M Wallenhorst

(57) ABSTRACT

A method of analyzing blood includes delivering a blood sample to a test device, applying a spatially varying electric field to the blood sample to provide a depleted cell concentration in a portion of the blood sample, and sensing a property of the portion of the blood sample.

24 Claims, 11 Drawing Sheets

U.S. PATENT DOCUMENTS

| | | |
|---|---|---|
| 6,193,866 B1 | 2/2001 | Bader et al. |
| 6,197,176 B1 | 3/2001 | Pethig et al. |
| 6,210,574 B1 | 4/2001 | Sammons et al. |
| 6,241,862 B1 * | 6/2001 | McAleer et al. ....... 204/403.05 |
| 6,264,815 B1 | 7/2001 | Pethig et al. |
| 6,287,832 B1 | 9/2001 | Becker et al. |
| 6,306,272 B1 | 10/2001 | Soane et al. |
| 6,310,309 B1 | 10/2001 | Ager et al. |
| 6,403,367 B1 | 6/2002 | Cheng et al. |
| 6,465,225 B1 | 10/2002 | Fuhr et al. |
| 6,518,034 B1 * | 2/2003 | Phillips et al. ................ 435/14 |
| 6,537,433 B1 | 3/2003 | Bryning et al. |
| 6,540,895 B1 | 4/2003 | Spence et al. |
| 6,596,143 B1 | 7/2003 | Wang et al. |
| 6,610,188 B1 | 8/2003 | Fuhr et al. |
| 6,641,708 B1 | 11/2003 | Huang et al. |
| 6,660,493 B2 | 12/2003 | Miles |
| 6,673,225 B1 | 1/2004 | Arnold |
| 6,685,812 B2 | 2/2004 | Miles |
| 6,727,451 B1 | 4/2004 | Fuhr et al. |
| 6,730,204 B2 | 5/2004 | Mariella, Jr. |
| 6,749,736 B1 | 6/2004 | Fuhr et al. |
| 6,761,811 B2 | 7/2004 | Mariella, Jr. |
| 2002/0005354 A1 | 1/2002 | Spence et al. |
| 2002/0036141 A1 | 3/2002 | Gascoyne et al. |
| 2002/0042125 A1 | 4/2002 | Peterson et al. |
| 2002/0055167 A1 | 5/2002 | Pourahmadi et al. |
| 2002/0076825 A1 | 6/2002 | Cheng et al. |
| 2002/0182627 A1 | 12/2002 | Wang et al. |
| 2002/0182654 A1 | 12/2002 | Jing et al. |
| 2003/0010637 A1 | 1/2003 | Cummings |
| 2003/0121788 A1 | 7/2003 | Gascoyne et al. |
| 2003/0134416 A1 | 7/2003 | Yamanishi et al. |
| 2003/0159932 A1 | 8/2003 | Betts et al. |
| 2004/0011652 A1 | 1/2004 | Bressler |

FOREIGN PATENT DOCUMENTS

| | | |
|---|---|---|
| WO | WO 97/34689 | 9/1997 |
| WO | WO 98/10869 | 3/1998 |
| WO | WO0212896 | 2/2002 |
| WO | WO 02/18933 | 3/2002 |
| WO | WO 02/29406 | 4/2002 |
| WO | WO0228523 | 4/2002 |
| WO | WO 03/014291 | 2/2003 |
| WO | WO 03/093496 | 11/2003 |

OTHER PUBLICATIONS

Tsuda, Takao, Yamauchi, Norihiro, and Kitagawa, Shinya, "Separation of Red Blood Cells at the Single Cell Level by Capillary Zone Electrophoresis", Analytical Sciences, vol. 16, pp. 847-850, (Aug. 2000).

Holmes, David and Morgan, Hywel, "Cell Positioning and Sorting Using Dielectrophoresis", European Cells and Materials, vol. 4, Suppl. 2, pp. 120-122, (2000).

* cited by examiner

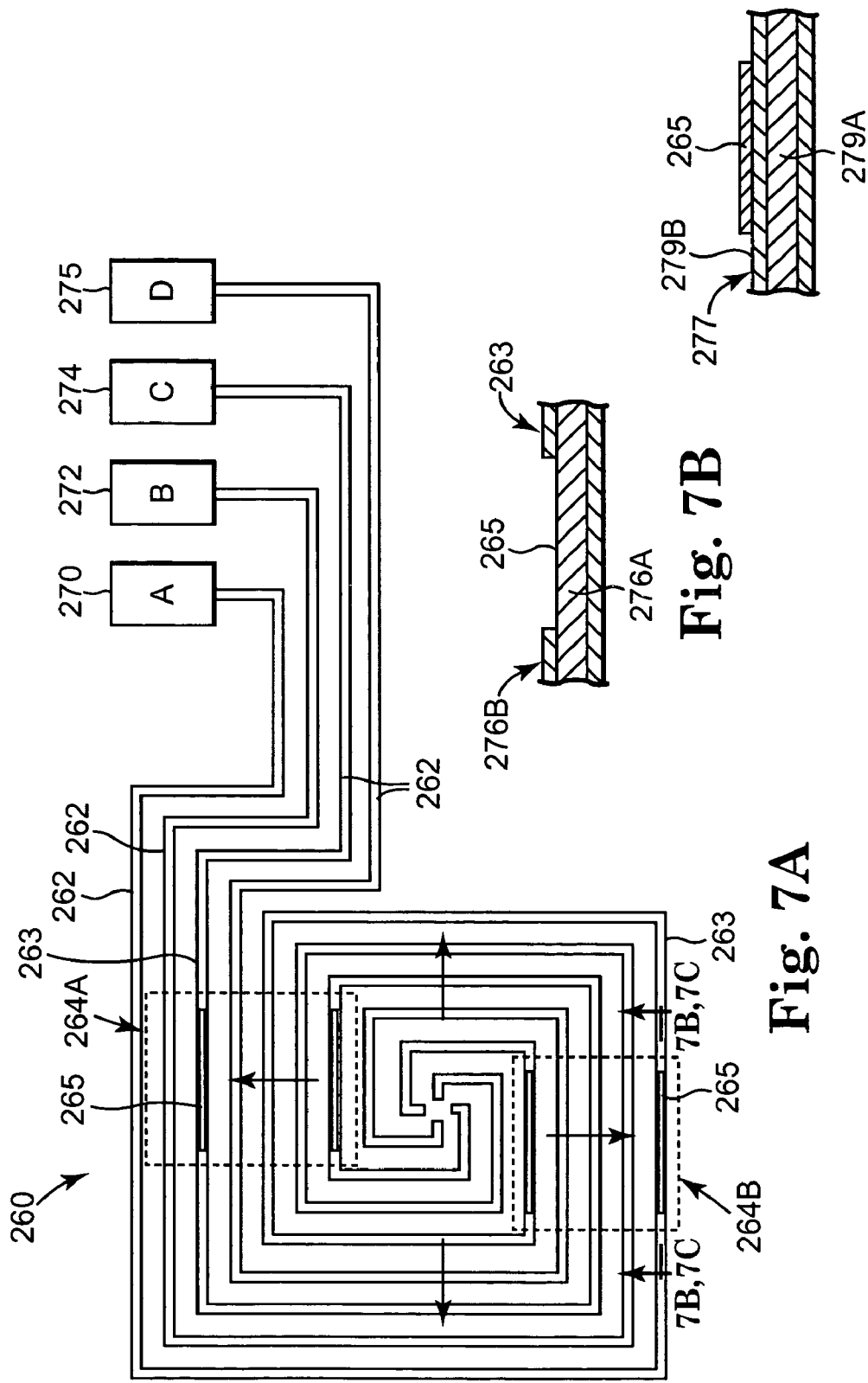

METHOD OF ANALYZING BLOOD

BACKGROUND

Millions of people across the globe face the daily challenge of managing their diabetes. Several times a day, they must test their blood for glucose levels. Currently, most consumers monitor their daily glucose levels by themselves through the use of electrochemical glucose meters. In these devices, a sample of blood is collected from a pin prick in the body into a test strip, which is inserted into a meter for calculation and display of the glucose level. The longevity and health of diabetics is directly related to how tightly their glucose levels are controlled through daily self-testing and administration of insulin, as well as diet and exercise. Accordingly, highly accurate glucose testing in self-monitoring can aid millions of diabetics who daily endeavor to maintain optimal blood glucose levels.

Moreover, since blood is a vital component of the body, many other blood analytes are of significant interest in managing human health. Accordingly, self-testing or measuring other components or properties of blood are also of interest as the medical industry seeks rapid and effective methods to monitor various medical conditions.

However, the speed and accuracy of conventional analyte detection is currently limited by difficulty in accessing the analyte of interest within the blood sample and difficulty in maximizing both chemical and optical/electrical interactions with the analyte under detection.

BRIEF DESCRIPTION OF THE DRAWINGS

FIG. 7A is a plan view schematically illustrating another electrode arrangement of a blood testing system, according to an embodiment of the present invention.

FIG. 7B is a sectional view of an electrode array as taken along lines 7B-7B of FIG. 7A, according to an embodiment of the present invention.

FIG. 7C is a sectional view of an electrode array as taken along lines 7C-7C of FIG. 7A, according to an embodiment of the present invention.

DETAILED DESCRIPTION

Figure 1:
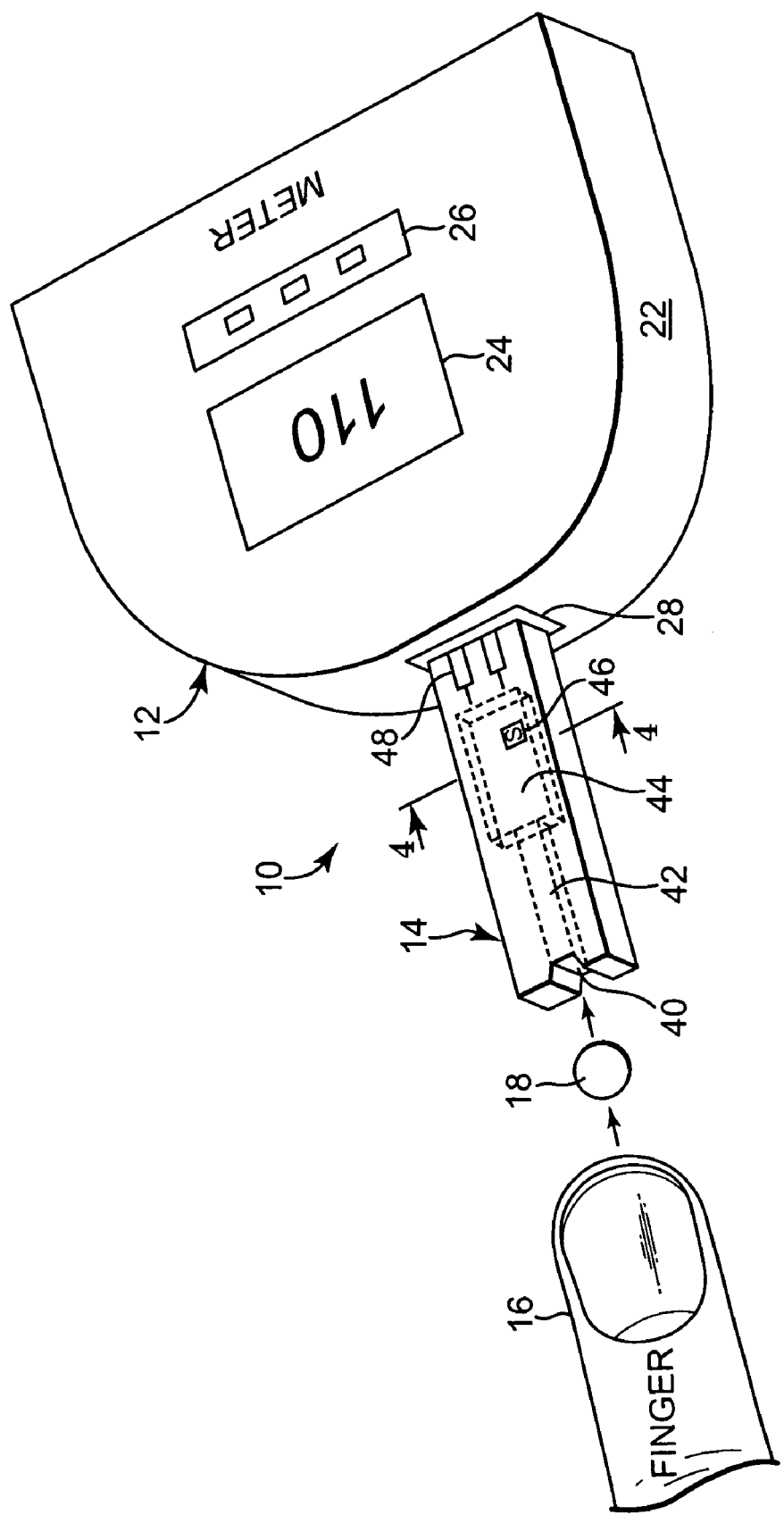
FIG. 1 is a perspective view of a blood testing system, according to an embodiment of the present invention.

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. Finally, although a flow chart in the figures of this application shows a specific order of execution, the order of execution may differ from that which is depicted. The following detailed description, therefore, is not to be taken in a limiting sense, and the scope of the present invention is defined by the appended claims.

Embodiments of the present invention are directed to a method for analyzing blood to detect an analyte or to determine a property of the blood. An analyte is any substance within a blood sample that is selected for detection. One blood analyte that can be measured indirectly through an electrochemical test includes glucose. In these tests, a sample of blood is exposed within a test strip to enzyme reagents for reaction with the glucose in the blood sample. The reaction products from the interaction of the blood glucose with the enzymes further interact with mediators and electrode sensors within the test strip as part of an electrochemical reaction. Based upon a measurement of current or charge at the electrode sensors from that electrochemical reaction, an indirect measurement of glucose concentration in the blood sample is obtained. Alternatively, the reaction products of the glucose-enzyme interaction are measured through reflectance photometry to indirectly determine a glucose level.

In one embodiment of the present invention, a sample of blood is delivered to a test device and a dielectrophoretic field is applied to the blood sample to cause a decreased cell concentration within a portion of the blood sample (i.e., a portion having a depleted cell concentration). A property of the blood is sensed in the decreased cell concentration portion of the blood sample to enhance measurement of the property of the blood. In other words, the dielectrophoretic field is applied to move cells in the blood sample away from the sensor(s) to enhance the measurement of analytes in the blood sample. In particular, this redistribution of cells within the blood sample exposes the sensor(s) to an enriched plasma region for analyte detection. This dielectrophoretic field can be applied to the blood sample before and/or during the measurement of a blood property or analyte.

A dielectrophoretic field can be defined as an electric field that varies spatially or is non-uniform where it is being applied to the particles (e.g., cells). Positive dielectrophoresis occurs when the particle (e.g., cell) is more polarizable than the medium (e.g., plasma) and results in the particle being drawn toward a region of higher field strength. A system operating in this way can be referred to as operating in a positive dielectrophoresis mode. Negative dielectrophoresis occurs when the particle is less polarizable than the medium and results in the particle being drawn toward a region of lesser field strength. A system operating in this way can be referred to as operating in a negative dielectrophoresis mode.

First, these electric fields are generated by applying a voltage between two or more electrodes. The field electrodes are disposed and arranged in a geometric relationship relative to one another to cause a non-uniformity or spatial variation in the applied electric field, which produces the dielectrophoretic effect. Accordingly, selectively applied variations in this geometric relationship of the field electrodes are used to cause desired movements of cells within the dielectrophoretic fields.

Second, by applying a time varying voltage to the field electrodes, a temporally varying electric field can be produced. This time variation will tend to affect the polarization of the fluid medium and the particles differently—hence it will affect the relative polarization between the fluid medium and the particles. Accordingly, selective application of time variance in the dielectophoretic field can be used to move cell particles in a desired manner.

In many cases, particularly where the variation is sinusoidal, the time variation has a characteristic frequency. The relative polarization of a particle relative to the medium is typically affected by the applied frequency. Large changes in frequency can be sufficient to change a system from operating in a negative dielectrophoresis mode to a positive dielectrophoresis mode. Stated another way for the case of red blood cells, there may be one frequency wherein the red blood cells move toward regions of higher field strength (the positive dielectrophoresis mode) and another frequency wherein the red blood cells move away from regions of higher field strength (the negative dielectrophoresis mode). Either negative or positive dielectrophoresis may be used in the embodiments of the present invention to move cells within a fluid medium such as plasma.

Third, when using more than two field electrodes, certain types of motion can be induced by selectively shifting which pair of electrodes has a voltage difference or using an amplitude modulation technique. For example, an arrangement of four interleaved and independent field electrodes can induce a "traveling wave dielectrophoresis" response in the particles to allow controlled translation of the particles.

With these dielectrophoretic parameters in mind, embodiments of the present invention use a dielectrophoretic field to enhance sensing a property of a blood sample by spatially redistributing cells in the blood sample. In particular, this spatial cell redistribution causes a greater proportion of plasma of the blood sample to be adjacent the sensor(s), which enhances the analyte measurement, making for a faster and potentially more accurate test.

Some embodiments of the present invention achieve improved analyte detection by overcoming the interference from cellular material in the blood that occurs in electrochemical analyte testing. This interference is primarily caused by the presence of red blood cells within the blood, which comprise a vast majority of cell bodies in blood. The level of red blood cells varies widely within and among individuals and depends upon many factors such as gender, various disease states, diet, and the altitude at which the person resides. Usually high levels of red blood cells (i.e., hematocrit) result in low glucose readings, and vice versa. Accordingly, the level of red blood cells in the blood significantly affects analyte testing.

In the context of electrochemical analyte detection, embodiments of the present invention overcome the interference of cell bodies in the blood to enhance several aspects of electrochemical analyte detection. First, removing cells (e.g., red blood cells) from the region of the sensor electrodes reduces the interference of the cells with the surface of the sensor electrodes. Removing these cells also decreases the viscosity of the blood sample in the region of the sensor electrodes, which in turn enhances diffusion of the blood analyte (e.g., glucose) and electron transfer mediators in the electrochemical cell. In particular, lower numbers of cell bodies (e.g., red blood cells, bacteria, etc.) enhance mechanical diffusion of plasma into reagent layers at which the analyte-enzyme reaction occurs, as well as facilitate free passage through the "holes" in various mesh membranes in the test strip, and effectively increase the volume of plasma (and analytes within the plasma) available to diffuse for reaction with the test enzymes. Furthermore, depletion of red blood cells reduces the presence of oxygen, which otherwise would compete deleteriously with an electron transfer mediator in common analyte measuring techniques. Accordingly, reduced oxygen concentrations, stemming from reduced red blood cell concentrations, result in more effective electrochemical measurements of the blood analytes.

Moreover, embodiments of the present invention can accommodate different types of electrochemical analyte detection while still minimizing the impact of cell bodies in the blood on accurate, quick detection. For example, in amperometry-based glucose sensing, sensor electrodes are spaced preferentially about 1 millimeter apart, in order to minimize diffusion of redox components (i.e., glucose-enzyme reaction components and products) between the sensor electrodes. In such an assay, movement of cells away from the surface of the sensor electrodes to a position between the sensor electrodes would reduce this diffusion of redox components and therefore enhance the glucose measurement. On the other hand, in coulometry-based glucose sensing, the sensor electrodes are spaced close together, preferentially on the order of 50-100 microns or less. This measurement technique relies on the diffusion of redox-active components between the sensor electrodes. With such methods, it is desirable to move the cells not only away from the surface of the sensor electrodes, but away from the region between the sensor electrodes as well. This cell redistribution will enhance diffusion processes between the electrodes, and therefore enhance the quality of the measurement as well. Accordingly, embodiments of the present invention can improve accuracy in different types of electrochemical detection by applying the dielectrophoretic field to reduce cell concentrations at the surface of the sensor electrodes as well as reducing cell concentrations between a plurality of sensor electrodes (e.g., coulometry-based glucose sensing) or outside a plurality of closely adjacent electrodes (amperometry-based glucose sensing).

Embodiments of the present invention can be applied for detection or measurement of many blood analytes other than glucose. Other common analytes of interest include, for example, markers for cardiovascular disease, drugs, illicit drugs, antibiotics, and antigens and toxins associated with infectious organisms. These analytes include, but are not limited to, troponins, b-type natriuretic peptide, clostridium difficile toxins, digitoxin, digoxin, theophylline, warfarin, barbiturates, methadone, amphetamine and amphetamine analogues, propoxyphene, opiates, cocaine, tetrahydrocannabinol, benzodiazepines, phencyclidine, gentamicin, vancomycin, acetyl choline, amylase, bilirubin, cholesterol, chorionic gonadotropin, creatine kinase, creatine, RNA, DNA, fructosamine, glutamine, hormones, ketones, lactate, peroxide, prostate-specific antigen, prothrombin, thyroid stimulating hormone, and their metabolites. U.S. Pat. No. 6,281,006 discloses methods to determine the concentration of RNA and DNA.

Finally, in some embodiments of the present invention, the sensor can comprise a light emitter/detector system (rather than an electrochemical sensor electrode system) to perform photometric analyte detection using immunoassay and fluorescence techniques. These techniques rely on photometric detection of a fluorescent signal, typically in the visible region of light. When immunoassay and fluorescence techniques are performed conventionally, red blood cells absorb and scatter light in the visible spectrum, and thus prohibitively interfere with analyte detection. Accordingly, conventional photometric analyte detection relies on filtration or centrifugation to remove the red blood cells prior to the analysis. However, embodiments of the present invention apply a dielectrophoretic field to alter the red blood cell concentration within the blood sample (without filtration or centrifugation) to minimize the interference of red blood cells. Accordingly, embodiments of the present invention enable faster photometric analyte tests, such as troponin analysis for detection of myocardial infarction, in which rapid analysis contributes to the subsequent treatment and well-being of the patient.

In addition, in some embodiments of the present invention analyte detection is performed on a blood sample that is substantially blood but that is not purely whole blood. For example, the blood sample can be a volume of whole blood that has been altered in some way to improve analyte testing, for example, by the addition of an anticoagulant or stabilizing agent. Common examples of such agents include EDTA, citrate, and heparin. EDTA stabilizes blood by binding the metal ions that would otherwise be available to proteases that degrade proteins. Citrate, like EDTA, binds metal atoms and can consequently retard proteolysis in blood. Heparin stabilizes proteins in blood samples. In addition, in some embodiments, the blood sample can be whole blood that has been partially filtered or otherwise sorted prior to delivery into a test device at which the dielectrophoretic field is applied Finally, depending on the relative conductivities of the cells (e.g., red blood cells) and the medium (e.g., plasma), application of a spatially varying electric field in some embodiments of the present invention may cause heating in the sample, which may enhance diffusion and the kinetics of the reaction of interest. This heating effect can be controlled by an appropriate choice of electronic conditions, so that the temperatures within the blood sample are suitable for the assays employed within the test device.

Accordingly, embodiments of the present invention enhance the measurement of a blood analyte such as glucose within a test device. This enhancement is accomplished by application of a spatially varying electric field which reduces cell concentrations in a portion of a blood sample where the measurement takes place, thereby preventing the displaced blood components from impeding various electrochemical analyte reactions or photometric analyte interactions.

In one embodiment shown in FIG. 1, system 10 is directed to testing blood properties, such as blood glucose levels, in blood sample 18 taken from a finger 16 or other body part of a human subject. System 10 comprises meter 12 and test strip 14. Meter 12 is generally a handheld-type glucose meter used by patients to assist in self-monitoring their glucose levels. However, meter 12 is not precluded from being used to measure and monitor other analytes and properties of blood obtained and detected via a test strip. Moreover, meter 12 also can comprise a countertop testing device rather than a handheld device.

Test strip 14 is removably insertable into a portion of meter 12 and comprises inlet 40, fluid pathway 42, chamber 44, sensor 46, and input/output contacts 48. Test strip 14 receives blood sample 18 into inlet 40 and fluid pathway 42 pulls blood sample 18 into chamber 44 via capillary fluid action through a combination of the fluid properties of blood and the dimensions, shape, and surface properties of pathway 42. Pathway 42 can have a cross sectional shape that is generally circular, generally triangular, generally rectangular or other shape suitable to inducing capillary action.

Chamber 44 of test strip 14 is an extension of fluid flow path defined by fluid pathway 42 and also acts as a reservoir for receiving and holding blood sample 18. Chamber 44 also comprises one or more enzyme or immunoassay reagents suitable for causing a chemical reaction or immunorecognition with an analyte in blood sample 18. This interaction creates a reaction product to enable indirect measurement of a blood analyte via an electrochemical or optical detection method.

Sensor 46 of test strip 14 is disposed within chamber 44 and is configured as an electrode or light emitter/detector for applying an electrochemical test or optical test, respectively, to determine a property of the blood, such as a blood glucose level. Finally, input/output contacts 48 of test strip 14 are electrically connected to sensor 46 and are exposed on a surface of test strip 14 to be removably insertable within receiver 28 of meter 12 for establishing electrical communication between test strip 14 and meter 12.

In some embodiments, test strip 14 is inserted into meter 12 prior to collecting blood sample 18 while in other embodiments, test strip 14 is inserted into meter 12 after collecting blood sample 18. In this latter case, test strip 14 can comprise a miniature power supply for supporting electrical functions within test strip 14 prior to electrical connection to meter 12.

Blood sample 18 collected by test strip 14 can be a sample of whole blood, as well as a sample of whole blood that is altered in some way to accentuate manipulation and testing of blood sample 18 within test strip 14. For example, a sample of whole blood can be altered through the addition of an agent to enhance the difference in relative polarization of the plasma and/or cellular components (e.g., red blood cells). Alternatively, the sample of whole blood can be manipulated by other techniques (prior to insertion into test strip 14) to render a blood sample 18 that excludes various components of the blood from the blood sample 18.

Meter 12 comprises housing 22, display 24, control panel 26, and receiver 28. Meter 12 includes housing 22 for enclosing system electronics to operate meter 12 and for supporting display 24 and control panel 26. Control panel 26 enables control of various functions of meter 12 directed at performing a test and/or evaluating results of a test on blood sample 18 performed within test strip 14. Display 24 provides a graphical representation of the test results and related information to the test consumer. Various aspects of meter 12, including system electronics carried therein, will be described in further detail in association with FIG. 2.

Figure 2:
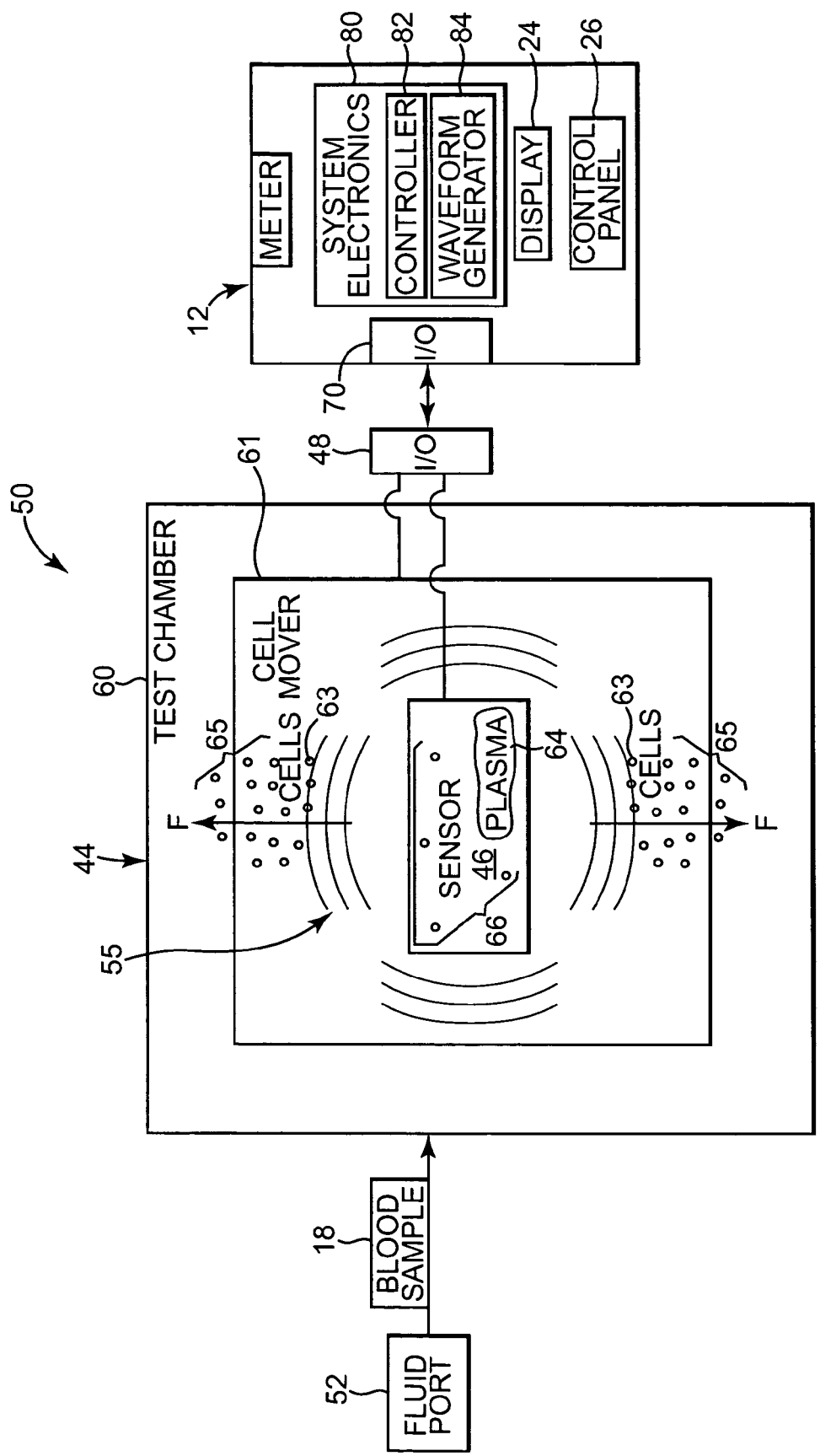
FIG. 2 is a plan view schematically illustrating a blood testing system, according to an embodiment of the present invention.

FIG. 2 is a schematic illustration of a system 50 which functionally represents system 10. As shown in FIG. 2, system 50 comprises fluid port 52, test chamber 44, and meter 12. Fluid port 52 represents fluid inlet 40 and fluid pathway 42 of FIG. 1. Test chamber 44 comprises container 60, cell mover 61, and sensor 46. Blood sample 18 generally fills container 60, and comprises cells 63 (e.g., red blood cells) and plasma 64. As shown in FIG. 2, components of blood sample 18, such as cells 63 and plasma 64, have been redistributed by force F applied by cell mover 61. This force F is imparted in one or more direction(s) by a spatially varying electric field 55 (e.g., a dielectrophoretic field), that when applied within blood sample 18, causes cells (e.g., red blood cells, bacteria) to move away from sensor 46 based on a relative position of sensor 46 and cell mover 61. After application of electric field 55, cells 63 are redistributed into a first portion 65 of blood having a relatively high concentration of a plurality of cells 63 and a second portion 66 of blood having a lower concentration cells 63.

Moving cells away from sensor 46 causes a relatively greater amount of plasma 64 to be adjacent sensor 46. This redistribution enables faster diffusion of glucose molecules for reaction with test enzymes in chamber 44 and faster migration of reaction products from the glucose-enzyme reaction to sensor 46. These dynamics are believed to increase the speed and/or accuracy of analyte detection.

Cell mover 61 comprises an electrode arrangement of one or more electrode elements or electrode arrays that are configured to create a spatially varying electric field to apply a dipole force to polarizable particles within a fluid medium. This field is sometimes referred to as a dielectrophoretic field, which causes a polarizable particle (e.g., cell) to respond with movement within the nonuniform electric field. In this embodiment cell mover 61 applies this spatially varying electric field to locally separate or to permanently separate components of blood, such as red blood cells, relative to other components within blood sample 18, such as plasma. This electric field can also be temporally varying to modulate polarization forces and/or to result in a traveling wave electric field, which further acts to impart movement of particles in the fluid medium being acted upon.

The direction of particle movement (e.g., red blood cell 63) within the fluid medium (e.g., blood sample 18) relative to cell mover 61 in response to the spatially varying electric field is typically referred to as negative dielectrophoresis or positive dielectrophoresis, depending upon the relative movement imparted by the electric field. The movement of particles or cells to a region of lower field strength is referred to as negative dielectrophoresis while the movement of particles or cells to a region of higher field strength is referred to as positive dielectrophoresis. This directional movement is affected by the presence, frequency, magnitude, and/or phase of the electric signal driving cell mover 61, as well as the conductivity of each blood component (e.g., red blood cells, plasma, white blood cells, platelets) relative to each other and the relative conductivity of the blood sample as a whole (e.g., the interaction of all blood components acting together as a single fluid medium). The direction, speed, and magnitude of particle movement within the fluid medium is also affected by the shape, size, and relative position of cell mover 61 in relation to the other parameters identified above. Directional movement of each particle can comprise any one or more of lateral movement (e.g., generally parallel), vertical movement (e.g., generally perpendicular), and/or a combination of lateral and vertical movement (e.g., radial inward or outward) relative to a surface of cell mover 61.

Accordingly, as further described in association with FIGS. 4-12, cell mover 61 can be implemented in a variety of field electrode arrangements that are placed in various positions within chamber 44 relative to sensor 46 to achieve the spatially varying electric field that moves cells 63 away from sensor 46. Moreover, with these varying parameters in mind, cell mover 61 is shown in FIG. 2 in a functional orientation for illustrative purposes to depict its interaction relative to sensor 46 and its impact on cells 63 within chamber 44, but cell mover 61 is not limited to the position or the geometric configuration shown in FIG. 2, nor are cells 63 limited to movement in the direction or position shown in FIG. 2.

As shown in FIG. 2, meter 12 comprises input/output contacts 70, system electronics 80, which includes among other components, controller 82 and waveform generator 84. Controller 82 directs various functions of meter 12 including operation of display 24 and control panel 26, while cooperating with waveform generator 84 to implement electric fields to be applied via cell mover 61 in chamber 44 of test strip 18. Waveform generator 84 enables alternating current waveforms operating at selectable magnitudes (e.g., voltages), frequencies, phases, and polarities (e.g., negative or positive frequencies). In some embodiments, waveform generator 84 is capable of generating signal frequencies in the range from DC to several Ghz.

In some embodiments because of the relative size and polarizability of cells (relatively large) and of analyte molecules (relatively small), a spatially varying electric field applied via cell mover 61 moves cells 63 within blood sample 18 without moving analyte molecules within blood sample 18 away from sensor 46.

Moreover, given that spacing between the field electrodes of cell mover 61 for producing the spatially varying electric field are on the order of 10 microns and waveform generator 84 produces a field of $10^5$ V/m or more, cells 63 are expected to move about 10-100 micrometers per second through the field, which corresponds to rapid movement of cells within a chamber of a test strip, which is sized on the order of microns.

System 50 can be operated in at least two different modes. In a pre-process mode, cell mover 61 manipulates blood sample 18 within chamber 44 to prepare blood sample 18 for a more accurate and/or faster measurement of a blood analyte in blood sample. In a sensing mode, sensor 46 of system 50 measures the property of the blood analyte, (e.g., blood glucose levels), during or after the pre-process mode. In some embodiments, the sensing mode can be performed to obtain a measurement prior to the pre-process mode, for example, prior to manipulating the distribution of components within the sample. This measurement can be compared with measurements that are taken during or after the pre-process mode.

Figure 3:
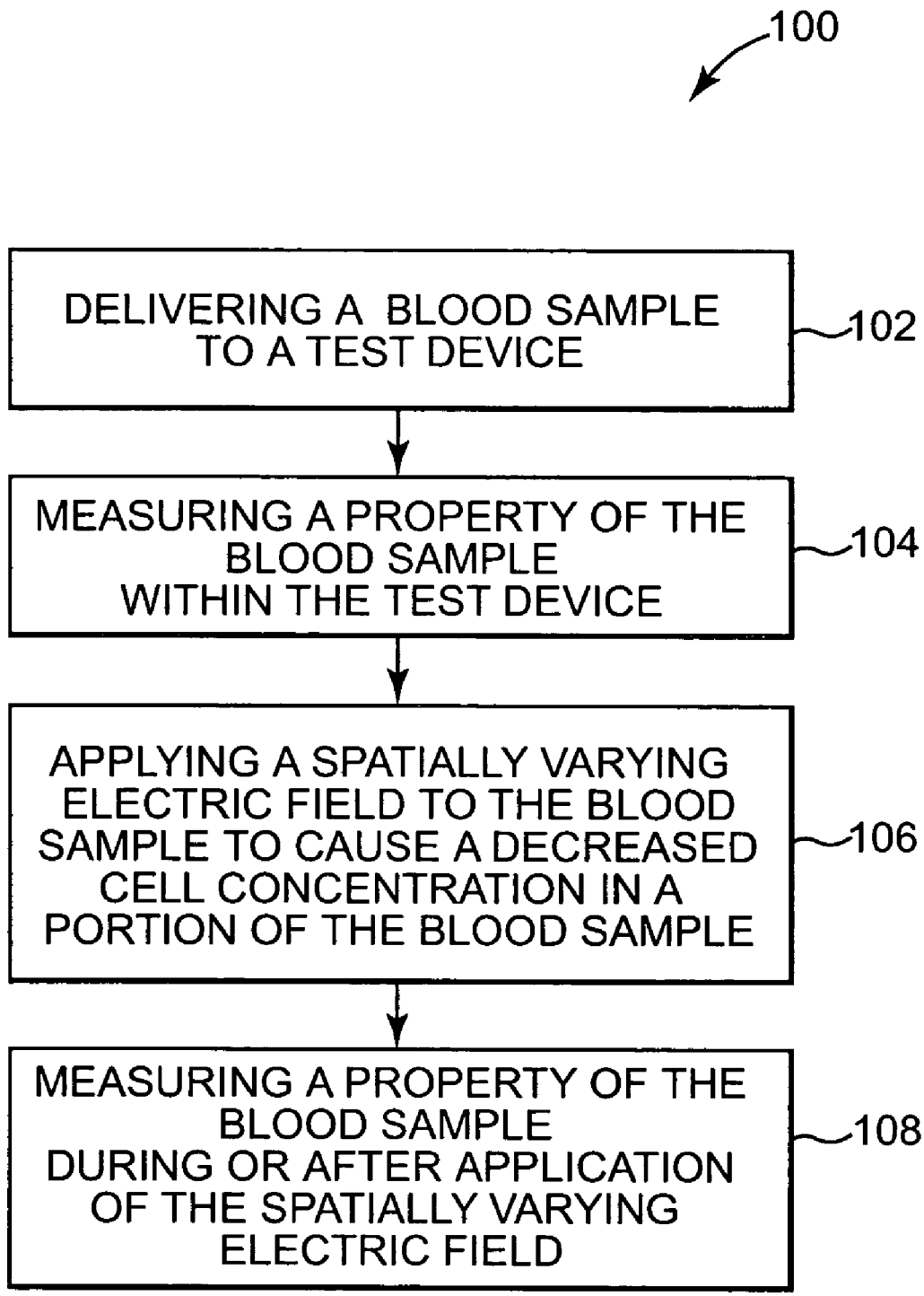
FIG. 3 is a block diagram of a method of testing blood, according to an embodiment of the present invention.

FIG. 3 illustrates a method 100 of analyzing a property of a blood sample. Systems 10 and 50 of FIGS. 1 and 2 are suitable for performing method 100, as well as other systems including components suitable for performing method 100.

As shown in box 102, method 100 comprises delivering a blood sample to a test device and then, as shown in box 104, measuring a property of the blood sample within the test device. This prior measurement establishes a baseline for comparison with later measurements in the method for establishing accuracy of the tests. As shown in box 106, method 100 also comprises applying a spatially varying electric field to the blood sample within the test device to cause a decreased cell concentration (i.e., depleted cell concentration) in a portion of the blood sample. This decreased cell concentration comprises a redistribution of cells to have a relatively lower concentration of cells adjacent a sensor and a relatively higher concentration of cells away from the sensor. With this change, a relatively greater amount of plasma that contains the analytes of interest is exposed to the sensors to enhance their detection. As shown in box 108, a property of the blood is measured during or after application of the spatially varying electric field, so that the measurement occurs when the cells are redistributed relative to the sensor.

In one embodiment, method 100 omits the activity in box 104 of measuring a property of the blood prior to applying the spatially varying electric field. Accordingly, in this embodiment, the property of the blood is measured only during or after the application of the electric field to the blood sample and not before applying the electric field.

Figure 4:
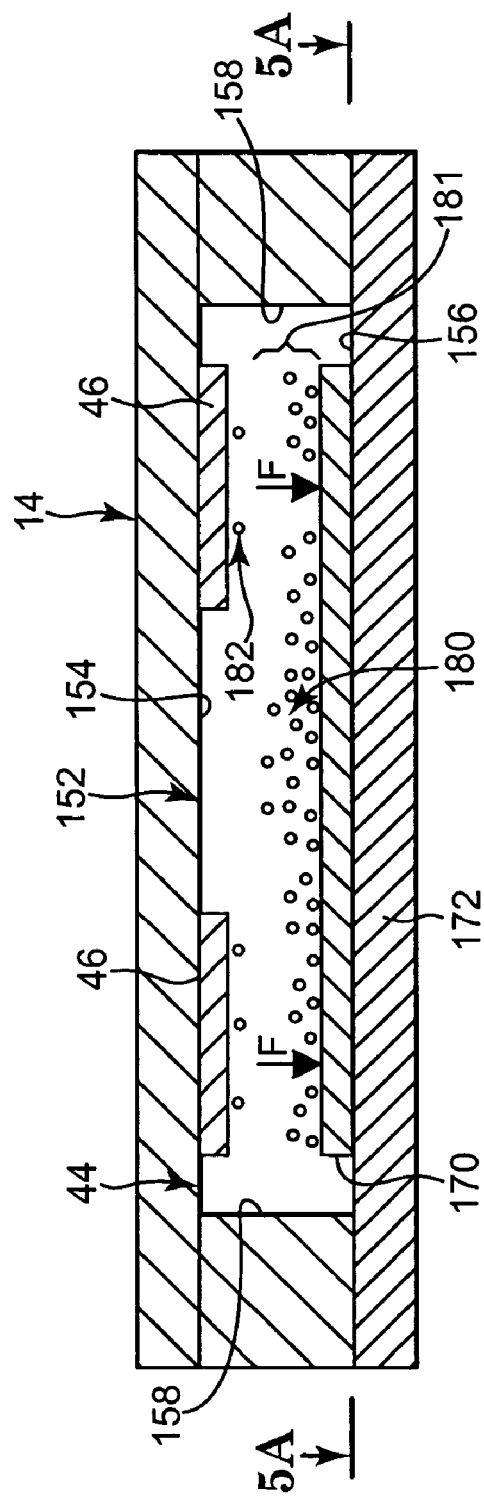
FIG. 4 is a sectional view of a test strip as taken along lines 4-4 of FIG. 1, according to an embodiment of the present invention.

FIG. 4 is a sectional view of test strip 14 of FIG. 1. FIG. 4 illustrates in more detail the structure and function of chamber 44 of test strip 14 as well as a redistribution of cells within chamber 44. As shown in FIG. 4, test strip 14 defines test chamber 44, which houses sensor(s) 46 and comprises top wall 154, bottom wall 156 defined by substrate 172, and opposing side walls 158. By way of illustrative embodiment, sensor(s) 46 comprise a pair of sensor electrodes configured for electrochemical testing of glucose and/or other properties of blood sample 18. Cell mover 170 is mounted on bottom wall 156, as defined by substrate 172 that supports and partially defines cell mover 170. Cell mover 170 comprises substantially the same features and attributes as cell mover 61, as previously described in association with FIG. 2.

FIG. 4 also depicts a redistribution of cells 180 from the effect or force applied (F) of the spatially varying electric field applied by cell mover 170. Upon redistribution of cells 180, a region 181 of higher concentrated cells 180 is disposed adjacent cell mover 170 and a region 182 of lower concentrated cells 182 is disposed adjacent sensor(s) 46. Region 181 is relatively enriched in cells 180 (e.g., red blood cells) while region 182 is relatively depleted of cells 180 (e.g., red blood cells), thereby enhancing analyte testing (e.g., glucose testing) at sensor(s) 46

Moreover, placing sensor(s) 46 on a roof (e.g., top wall 154) of chamber 44 enables gravity to also bring cells 180 downward away from sensor(s) 46. However, in another arrangement, sensor(s) 46 and cell mover 170 can be switched so that cell mover 170 is located on a roof (e.g., top wall 154) of chamber 44 and sensor(s) 46 is disposed on bottom wall 156 of chamber 44.

Force F represents a force component exerted upon cells 180 by the spatially varying electric field applied by cell mover 170 within the blood sample in chamber 44 that forces cells 180 away from sensor 46. As previously described in association with FIG. 2, a frequency, magnitude, and phase of the electric field, as well as relative conductive properties of the plasma and cells of the blood sample determine a direction and speed by which the cells move. While accounting for these parameters, waveform generator 84 of system electronics 80 in meter 12 (FIG. 2) energizes cell mover 170 with an electrical signal suited to imparting the desired electric field. Examples of various electrode arrangements capable of acting as cell mover 170 within chamber 44 are described in association with FIGS. 6A-6C and 8.

Figure 5B:
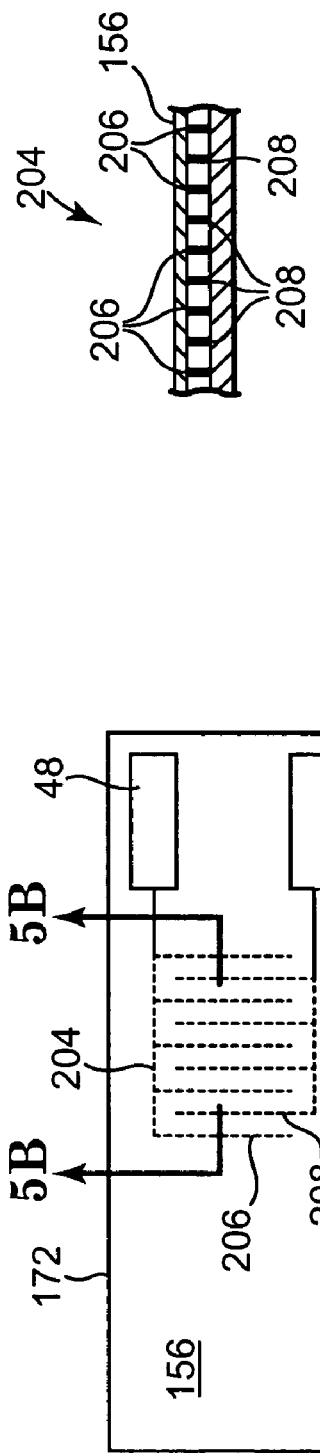
FIG. 5B is a sectional view of a test strip as taken along lines 5B-5B of FIG. 5A, according to an embodiment of the present invention.
Figure 5A:
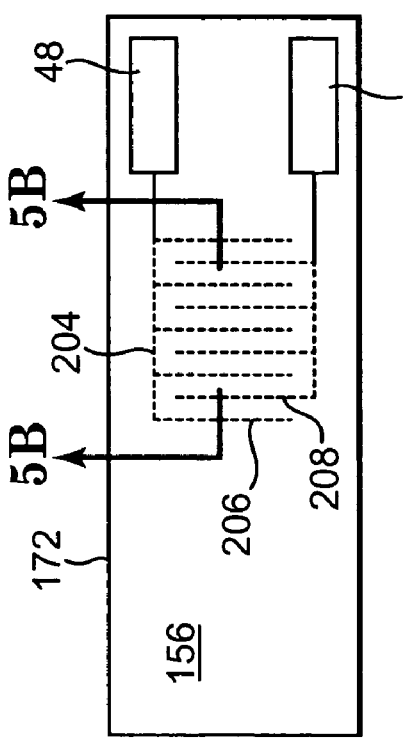
FIG. 5A is a sectional view of a test strip as taken along lines 5A-5A of FIG. 4, according to an embodiment of the present invention.

FIG. 5A is a sectional view of FIG. 4, representing another embodiment in which cell mover 170 on top of substrate 172 is replaced by electrode array 204 disposed within substrate 172 to move cells. Electrode array 204 is shown in phantom by dashed lines to represent its position below a top surface of substrate 172, which defines bottom wall 156 of chamber 44. As shown in FIG. 5A, electrode array 204 comprises a plurality of interdigitated (or interleaved) electrode elements 206 and 208, with each electrode element having multiple fingers that are interposed with each other. Each finger is spaced from each other on the order of about 10 microns. Each electrode element 206 and 208 is connected to one of input/output contacts 48. To deplete the cells (e.g., red blood cells) near sensor 46, electrode array 204 is operated in a positive dielectrophoresis mode to draw the cells away from sensor 46. Stated another way, the interdigitated arrangement of electrodes provide a relatively high electric field region in the vicinity of electrode array 204 relative region near sensor 46. The operating frequency is selected such that the red blood cells are more polarizable than the medium, resulting in a net force F tending to drive the cells away from the sensor 46 and toward the electrode array 204.

FIG. 5B is a sectional view of FIG. 5A showing additional detail of electrode array 204. As shown in FIG. 5B, electrode array 204 (elements 206, 208) is disposed just below a surface of wall 156, which acts as an insulator, so that electrode elements are not directly exposed within chamber 44. This arrangement is in contrast to FIG. 4, in which electrode elements comprising cell mover 170 are directly exposed to blood within chamber 44.

In another embodiment, the interdigitated electrodes of FIG. 5B can be placed in direct contact with the fluid in chamber 44. In other embodiments, electrode array 204 can be replaced with other electrode arrays, such as those electrode arrays shown in FIGS. 6A-6C.

Figure 6A:
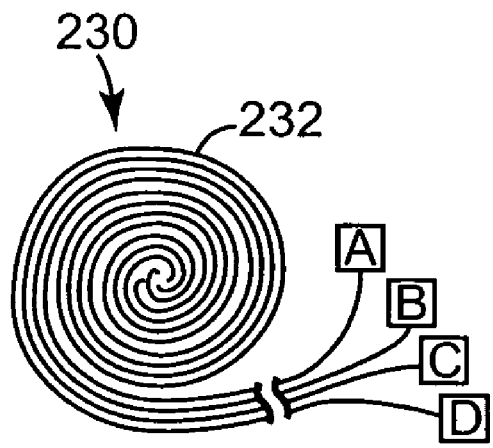
FIG. 6A is a plan view schematically illustrating an electrode arrangement of a blood testing system, according to an embodiment of the present invention.
Figure 6B:
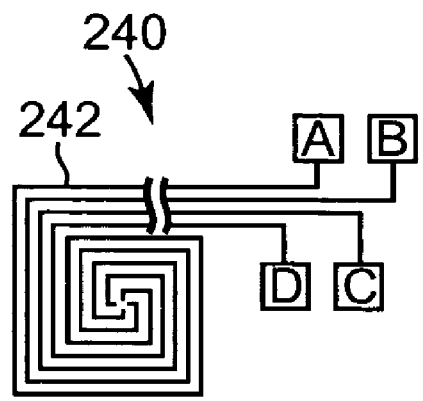
FIG. 6B is a plan view schematically illustrating an electrode arrangement of a blood testing system, according to an embodiment of the present invention.
Figure 6C:
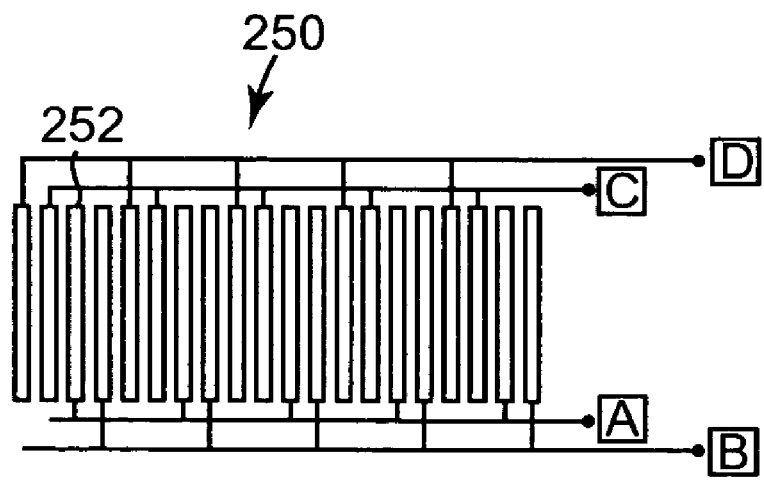
FIG. 6C is a plan view schematically illustrating an electrode arrangement of a blood testing system, according to an embodiment of the present invention.

FIGS. 6A-6C illustrate various electrode arrays for applying a spatially varying electric field within a test chamber on a blood sample to redistribute cells within the blood sample in the test device. Based on their geometry, these electrode arrays are also capable of adding a traveling wave effect to the polarizing effect on the cells. In addition, while accounting for the other parameters of a spatially varying electric field (e.g., signal frequency, signal magnitude, signal phase, particle size, particle polarizability, fluid medium polarizability, etc), each of these electrode arrays can be used to create a negative dielectrophoresis or positive dielectrophoresis effect on the red blood cells or other blood components. One or more of these electrode arrays can be used as cell mover 61 in system 50 in FIG. 2 and/or cell mover 170 in chamber 44 of FIG. 4.

FIG. 6A shows a spiral electrode array 230 comprised of a plurality of electrode elements 232 arranged in a spiral, which thereby permit applying a spatially varying electric field to attract or repel polarizable particles within a fluid medium relative to the surface of spiral electrode array 230 in a generally radial direction. In one embodiment, spiral electrode array 230 moves cells within a blood sample relative to other blood components, such as plasma which contains glucose, thereby enabling redistribution of cells relative to a sensor within a test device (e.g., test strip). As shown in FIG. 6A, spiral electrode array 230 also comprises four distinct electrode elements arranged concentrically together which can correspond to four distinct signal channels (e.g., A, B, C, D). These distinct channels enable independent driving of the four electrode elements to create a traveling wave that moves particles (e.g., red blood cells) laterally across surface of spiral electrode 230.

FIG. 6B shows nested electrode array 240 comprised of a plurality of electrode elements 242 arranged in a generally square-shaped nested array that permits applying a spatially varying electric field to attract or repel polarizable particles (within a fluid medium) generally perpendicular to electrode array 240. In one embodiment, nested electrode array 240 attracts or repels red blood cells within a blood sample relative to other blood components, such as plasma which contains glucose, thereby enabling redistribution of cells within a chamber relative to a sensor. As shown in FIG. 6B, nested electrode array 240 also comprises four distinct electrode elements arranged in an alternating manner together which can correspond to four distinct signal channels (e.g., A, B, C, D). Accordingly, in some embodiments, nested electrode array 240 allows independent driving of the four electrodes to create a traveling wave that moves particles (e.g., red blood cells) laterally across surface of nested electrode array 240 in directions generally perpendicular to the electrodes. In one embodiment, corners defined by portions of each electrode element 242 may have a radius to reduce high field effects at the corners.

FIG. 6C shows linear electrode array 250 of electrode elements 252 for applying a spatially varying electric field in a traveling wave. As shown in FIG. 6C, every fourth electrode element is linked together to form a signal channel (e.g., channel A) to permit activating and deactivating those linked elements together as a single unit. By repeating this arrangement, all of the electrode elements 252 are distributed into four operational sets in which each set is defines a channel to enable four distinct signal channels to be applied to electrode array for implementing independent driving of each of the four operational sets. Accordingly, like electrode arrays 230 and 240, linear electrode array 250 enables application of a traveling wave in a spatially varying electric field.

FIG. 7A is a plan view depicting a generally square-shaped nested electrode array 260 comprising four distinct electrode elements 262. Electrode array 260 is configured for placement within test device, such as chamber 44 of FIG. 4. Electrode array 260 is configured for both applying a traveling wave electric field to move cells, and for sensing blood analyte levels in portions of blood remaining adjacent electrode array 260 after (or during) removal of cells away from portions of electrode array 260.

The traveling wave electric field applied via electrode array 260, moves cells (e.g., red blood cells) along a surface of electrode array 260 in a direction perpendicular to the electrode elements 262.

In addition, electrode array 260 includes sensor zones 264A, 264B configured for measuring a property of blood or blood analytes, such as glucose, through electrochemical testing. Each sensor zone 264A, 264B comprises one or more sensors 265. In particular, some electrode elements 262 of electrode array 260 are modified into a hybrid element 263 that is a combination of a field electrode 262 used to generate the spatially varying electric field and a sensor portion 265 acting as a measurement electrode. This hybrid element 263 can be used to impart the spatially varying electric field and/or to measure a property of the blood. Sensor portion 265 is constructed in the manner shown in FIGS. 7B and 7C, as will be described below.

In one arrangement, each field electrode 262 of array 260, including hybrid elements 263 is first activated to move cells (e.g., red blood cells) in the spatially varying electric field (generated via electrode array 260) away from sensor portions 265. After or during this redistribution of cells away from sensor portions 265, field electrode 262 and hybrid electrode elements 263 are deactivated, except for sensor portions 265 of each hybrid element 263 which are activated to measure a property of the blood (e.g., glucose) that remain adjacent to, and are exposed to, sensor portions 265. In this way, a single hybrid electrode element 263 is provided to take the place of having separate sensor electrodes and field electrodes within a test device. This combination may be desirable to save space or to effectively move the bulk of the cells or other particles away from sensor portions 265.

Electrode array 260 is shown in FIG. 7A in a simplified form for illustrative purposes to depict how the four elements are nested together in a repeating pattern. In some embodiments of electrode array 260, these four elements can be nested from 2 or 3 levels of nesting up to 15 or more levels of nesting. The degree of nesting depends upon the size of the chamber, as well as the magnitude of the electric field to be generated. Also, the electrode elements may include radiuses to eliminate sharp corners and hence high field regions to improve operational efficiency. This is not shown for simplicity.

FIGS. 7B and 7C are sectional views of FIG. 7A which show a construction of hybrid electrode element 263 (FIG. 7B) and hybrid electrode element 277 (FIG. 7C), respectively. In one embodiment as shown in FIG. 7B, hybrid electrode element 263 comprises conductor 276A with outer layer 276B which is partially removed to expose a portion of conductor 276A to define sensor portion 265. In another embodiment, as shown in FIG. 7C, hybrid electrode element 277 comprises conductor 279A with outer layer 279B having sensor 265 disposed on a surface of outer layer 279B.

Accordingly, electrode array 260 of FIG. 7A (and supporting FIGS. 7B, 7C) enables both moving blood components relative to a sensor and/or sensing blood components in systems and methods of the present invention to enhance measurement of a property of blood.

Figure 8:
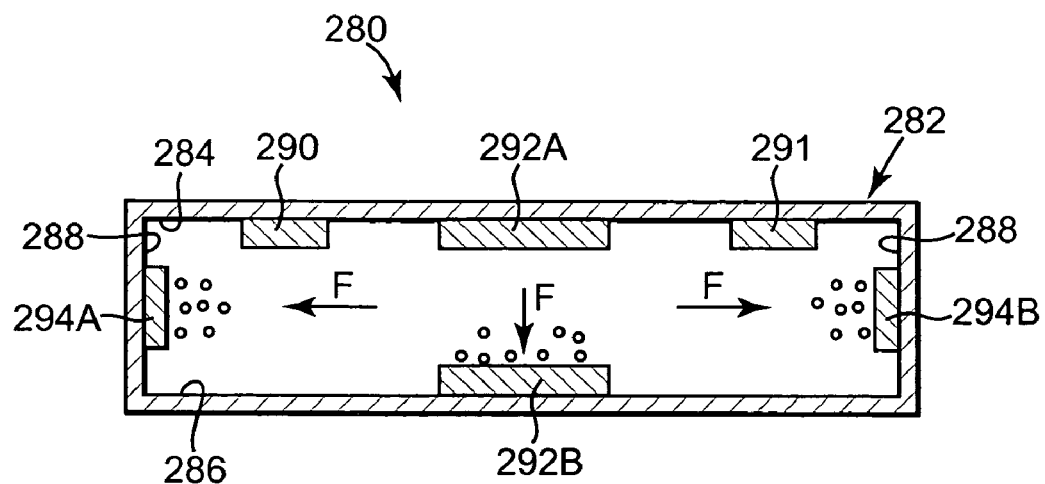
FIG. 8 is a sectional view of another test device of a blood testing system, according to an embodiment of the present invention.

FIG. 8 is a sectional view of atest strip 280 having a configuration substantially the same as test strip 14 of FIG. 4, except showing varying arrangements of electrodes and sensors within test chamber 282. Test chamber 282 comprises top wall 284, bottom wall 286, and opposing side walls 288. As shown, sensors 290 and 291 are mounted on top wall 284 while electrode array 292A is mounted on top wall and electrode array 292B is mounted on bottom wall 286. Electrode arrays 294A and 294B are mounted on each of opposing side walls 288, respectively. However, chamber 280 is not limited to the configuration of electrode elements shown in FIG. 8. Each of electrode arrays 292A, 292B, 294A, 294B can comprise a single electrode element or a plurality of electrode elements configured as one of the electrode arrays previously described.

In one embodiment, electrodes 294A and 294B are omitted from side walls 288 and only one electrode array (either electrode array 292A or 292B) configured as a plurality of electrode elements acts to impart the spatially varying electric field on the blood within chamber 282 to draw cells to electrode array 292A or 292B and thereby away from sensor 290.

In another embodiment, one of electrode array 292A (on top wall 284) or electrode array 292B (on bottom wall 286) can comprise a single electrode element in combination with another single electrode element for producing a spatially varying electric field. For example, electrode array 292B on bottom wall can act as one dipole of the electric field while electrode array 292A is positioned on top wall 282 to act as the complementary dipole of the electric field. By applying a suitable waveform from a waveform generator, a spatially varying electric field is created between electrode arrays 292A and 292B.

In another embodiment, electrode arrays 292A and 292B are omitted from top wall 284 and bottom wall 286, and electrode arrays 294A and 294B are used to apply the spatially varying electric field to draw cells laterally toward side walls 288, and thereby away from sensor 290. Each electrode array 294A and 294B can operate independently so that each electrode array 294A and 294B acts to pull cells away from sensor(s) 290, 291 with its own spatially varying electric field. Alternatively, electrode arrays 294A, 294B can operate together to create a single spatially varying electric field that move cells in one direction laterally toward a single side wall away from sensor(s) 290, 291.

In other embodiments, one of the electrode elements 292A, 292B are omitted and one of the electrode elements 294A, 294B from side walls 288 are omitted. In this arrangement, one electrode element (either 292A or 292B) is located on at least one of the top wall and the bottom wall, and one electrode element (either 294A, 294B) is located on at least one of the side walls 288 (but not both). A spatially varying electric field is produced between an electrode on a side wall and an electrode that is on either a top wall or a bottom wall, causing cells to be moved away from sensor(s) 290, 291 to enhance a measurement of a property of the blood at sensor(s) 290, 291. With a signal applied at the electrodes in this arrangement having a suitable frequency, magnitude, phase, etc., this electrode arrangement also can induce electrorotation of polarizable particles within chamber 280 to enhance mixing and reaction of those components to enhance the speed and/or accuracy of the test.

Finally, sensors 290, 291 are not limited to being located on top wall 284 of chamber 282. For example, in some embodiments, sensors 290, 291 can be located on bottom wall 286, or even side walls 288. In addition, one sensor 290 can be located on a bottom wall or top wall, while the other sensor 291 can be located on a side wall 288.

In embodiments of FIG. 8, a pair of electrode elements or one or more electrode arrays are positioned within chamber 280 on one or more walls within sufficient proximity to sensors 290, 291 to cause cells, such as red blood cells, to move within a spatially varying electric field away from sensor(s) 290, 291 to enhance measurement of a property of blood (e.g., glucose) at sensor(s) 290, 291.

Figure 9:
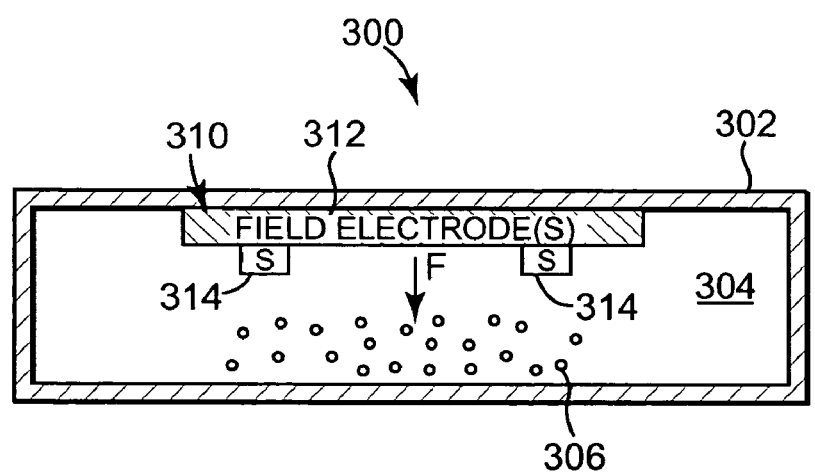
FIG. 9 is a sectional view of another test device of a blood testing system, according to an embodiment of the present invention.

In another embodiment of FIG. 8, all field electrodes and sensor electrodes are eliminated except for a pair of electrodes disposed on a top wall 284 (e.g. roof) designated by 292A. This embodiment is illustrated schematically in FIG. 9. As shown in FIG. 9, system 300 comprises chamber 302, plasma 304, cells 306, electrode arrangement 310 including field electrode(s) 312 and sensor electrode(s) 314. In one embodiment, electrode arrangement 310 comprises a single array of electrode elements including both a field electrode component and a sensor electrode component.

In use, a waveform is applied via field electrode 312 to produce a dielectrophoretic field that drives cells 306 away from sensor electrode(s) 314 to produce a reduced cell concentration within plasma 304 in chamber 302. Next, sensor electrodes 314 of electrode arrangement 310 are activated to detect an analyte within the portion of the blood sample adjacent to sensor electrodes 314 that is relatively depleted of cells 306. Accordingly, a single electrode array disposed on a roof of a test chamber is used to both repel cells away from the roof and then measure an analyte adjacent the roof in a reduced cell concentration region. While this single electrode array can be disposed on a side wall or bottom wall, a roof location also enables gravity to pull cells downward away from the single electrode array in chamber 302.

In one embodiment, field electrode 312 (e.g., electrode 292A in FIG. 8) comprises an interdigitated electrode pair substantially similar to that depicted in FIG. 5A except that electrode pair 292A is in contact with the blood. In operation, the electrode pair 292A is first used to repel the red blood cells in a negative dielectrophoresis mode. During and/or after this, two or more electrode elements 206, 208 of electrode array 204 of FIG. 5A are used as an electrochemical sensor. Each element 206, 208 of electrode array 204 is adapted to have substantially the same construction as hybrid elements 263 (FIG. 7A-7C) which have a field electrode and a sensor electrode combined into a single electrode element.

In another embodiment, electrode arrangement 310 of FIG. 9 comprises electrode array 250 of FIG. 6C. This electrode array 250 is operated to produce a travelling wave negative dielectrophoretic field on cells 306. Electrode array 250 is adapted to have the hybrid construction of combined field electrodes and sensor electrodes, substantially similar to the construction described and illustrated in FIGS. 7A-7C.

Figure 10:
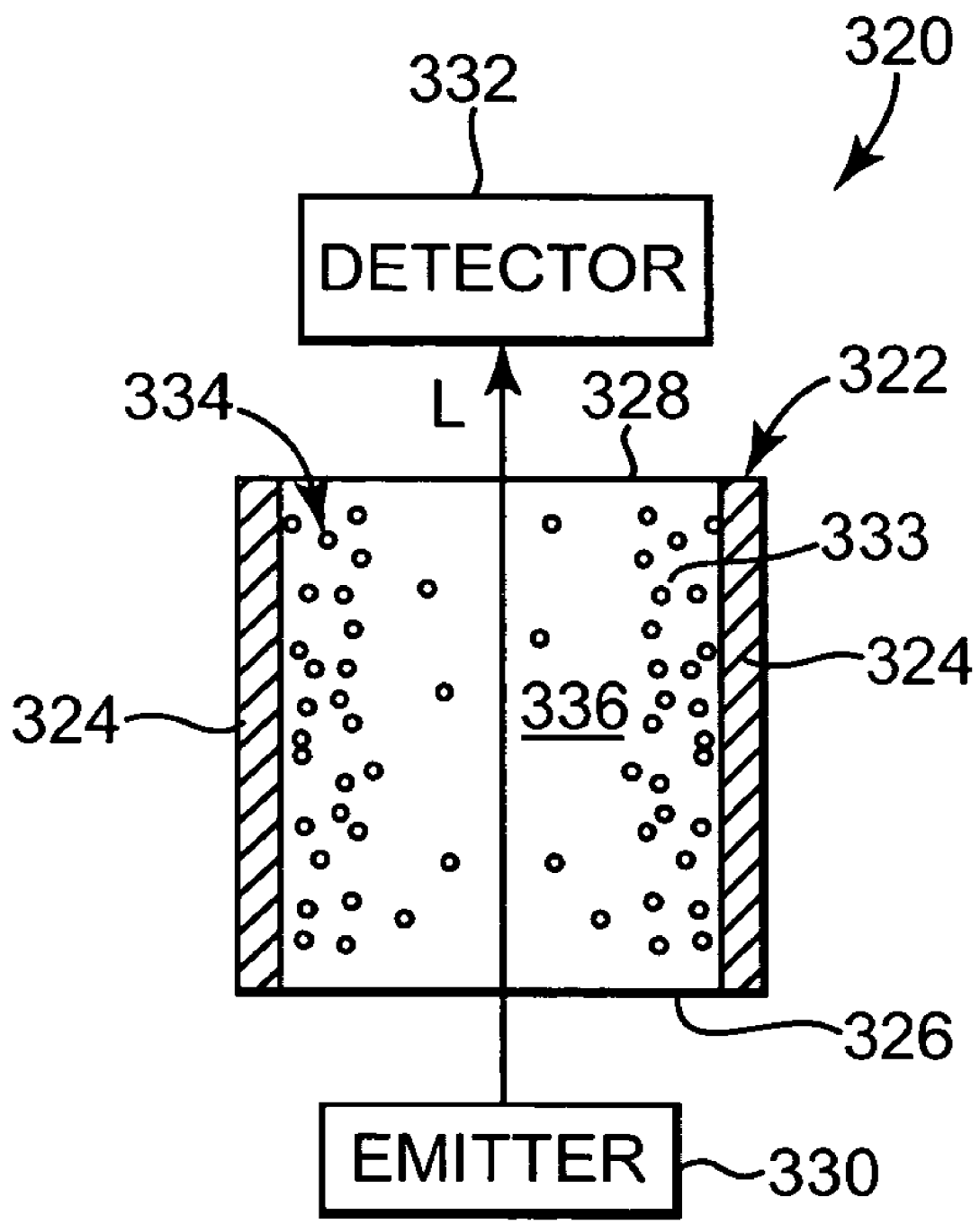
FIG. 10 is a schematic illustration of another test device of a blood testing system, according to an embodiment of the present invention.

FIG. 10 is a sectional schematic view of another embodiment of a test chamber of a test strip with an optical sensor. In this embodiment, an optical sensor 320 replaces electrochemical sensor 46 previously described in some of the embodiments of test chambers of test strips in FIGS. 1-9. In particular, FIG. 10 shows test chamber 322 with optical sensor 320 having emitter 330 and detector 332. Emitter 330 directs light through transparent bottom wall 326 and transparent top wall 328 to enable reflectance photometry testing of a property of a blood analyte, such as glucose. Other analytes that are detectable with the system of FIG. 10 include, but are not limited to, troponin analysis for detection of myocardial infarction, as well as one or more of the analytes previously identified in connection with photometric testing, and immunoassay/fluorescence analyte detection.

Electrode arrays 324 capable of causing a spatially varying electric field (e.g. electrode elements or electrode arrays of FIGS. 1-8) define opposed side walls of chamber 322. With the application of a spatially varying electric field, cells 333 are attracted to electrodes 324 through positive dielectrophoresis, thereby causing a region 334 of higher concentration of red blood cells 333 and a region 336 of lower concentration of red blood cells 333, through which light L between emitter 330 and detector 332 passes for determining glucose levels through reflectance testing. In this way, red blood cells are redistributed in the test chamber relative to a sensor (or relative to a spatially varying electric field) to enhance measuring a property of blood, such as glucose.

Finally, in some embodiments emitter 330 and detector 332 are disposed on a test strip, such as test strip 14. In other embodiments, emitter 330 and detector 332 are disposed on a portion of a meter (e.g., meter 12 shown FIGS. 1-2) such that upon insertion of the test strip into the meter, emitter 330 and detector 332 are disposed about chamber 322 to perform the reflectance photometry test on the blood sample within chamber 322.

Figure 11:
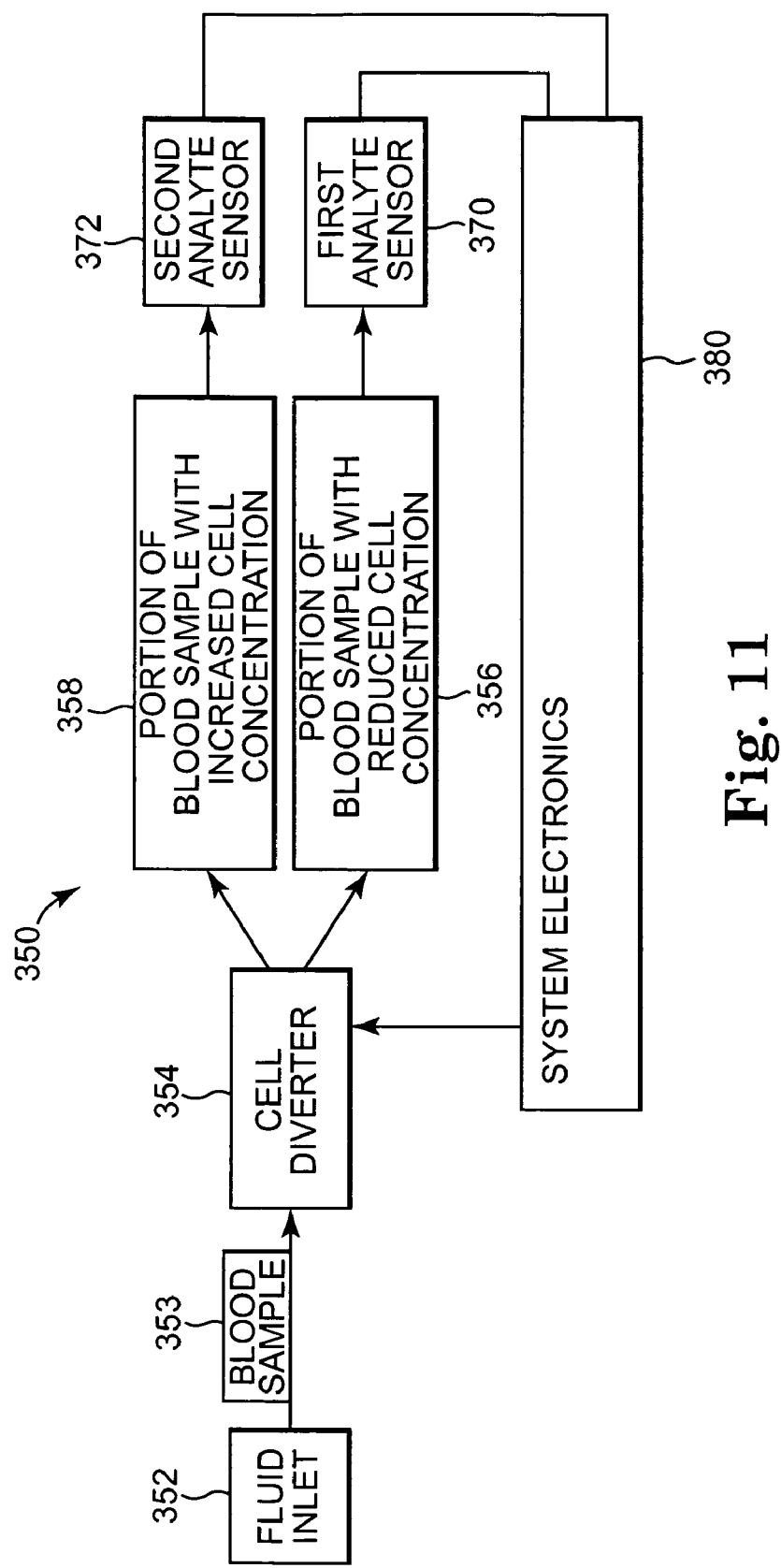
FIG. 11 is a plan view schematically illustrating another blood testing system, according to an embodiment of the present invention.

FIG. 11 is a schematic illustration depicting system 350 which enhances testing of blood analytes, such as glucose, in a blood sample by excluding a portion of cells, such as red blood cells, from the rest of the blood sample. In other words, a portion of cells is diverted from the blood sample prior to testing for an analyte. The blood sample can be whole blood, or whole blood that is altered by removal of some blood components or by addition of agents to enhance testing of the blood sample.

As shown in FIG. 11, system 350 comprises fluid inlet 352, cell diverter 354, first chamber for a first portion 356 of blood, second chamber for a second portion 358 of blood, first analyte sensor 370, second analyte sensor 372, and system electronics 380. Fluid inlet 352 is a port for receiving blood sample 353 and delivering blood sample 353 to other operative elements of system 350. Cell diverter 354 acts on the red blood cells within blood sample 353 to divert cells (e.g., red blood cells) within blood sample 353 relative to the other components of the blood sample 353 to create the first portion 356 of blood that has a reduced cell concentration (relatively depleted of cells). Consequently, the second portion 358 of blood sample 353 has an increased cell concentration (relatively enriched in cells). This second portion 356 therefore has a relatively higher concentration of plasma (relative to cells) which facilitates reaction of an analyte (e.g., glucose) within the enzyme test reagents and facilitates the electrochemical detection of the analyte, since the presence of the potentially interfering cells is minimized, as previously described.

The relatively depleted first portion 356 of cells is exposed to first analyte sensor 370 for measurement of a property (e.g., glucose) of portion 356. In some embodiments, the relatively enriched second portion 358 of cells is exposed to second analyte sensor 372 for measurement of a property (e.g., glucose) of portion 358 and then the measured properties of portions 356 and 358 of blood sample 353 are compared to evaluate the accuracy of the measurements. However, in other embodiments, the relatively enriched second portion 358 of red blood cells is not exposed to second analyte sensor 372 for measurement of any of its properties, and therefore no comparison is made to the properties measured within relatively depleted second portion 356.

Cell diverter 354 comprises an electrode arrangement including one or more electrode elements or electrode arrays capable of imparting a spatially varying electric field on cells to cause a separation of blood sample 353 into the first portion 356 and the second portion 358.

System electronics 380 carries substantially the same features and attributes as system electronics 80, as previously described in association with FIGS. 1-2, and therefore includes similar components such as a controller, waveform generator, etc. System electronics 380 is in electronic communication with cell diverter 354 to control the operation of cell diverter 354. System electronics 380 is also in electrical communication with first analyte sensor 370, and second analyte sensor 372 to control operation of sensors 370, 372 and to receive measurement data from electrochemical sensing of blood properties (e.g., glucose) by sensors 370, 372.

Figure 12:
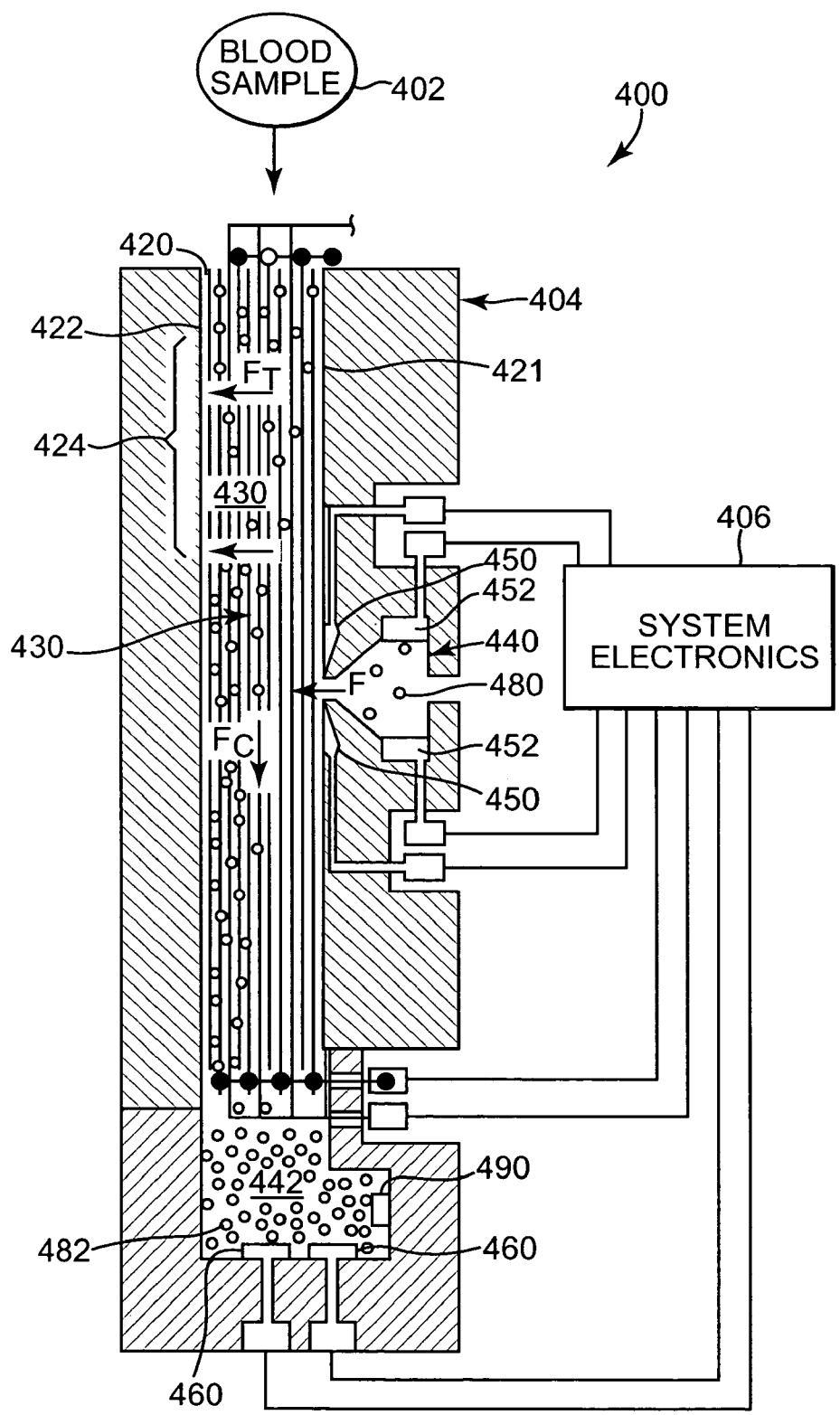
FIG. 12 is a sectional view of a test strip of a blood testing system, according to an embodiment of the present invention.

FIG. 12 is a sectional view of an example embodiment of system 400, which represents one embodiment of system 350 of FIG. 11. Accordingly, system 400 is directed to enhancing measuring a property of the blood, such as glucose, by redistributing cells relative to a sensor via application of a spatially varying electric field to the blood sample within a test device (e.g., a disposable test strip). In particular, system 400 is directed to diverting cells (e.g., red blood cells, bacteria) within a blood sample into one of two chambers to separate and exclude cells from the remainder of the blood sample.

As shown in FIG. 12, system 400 comprises blood sample 402 for testing in test strip 404 with system electronics 406. Test strip 404 comprises fluid path 420 defined by first side wall 421, second side wall 422, and field electrode array 430 extending through fluid path 420. Fluid path 420 also comprises a conduit portion 424 (e.g., entrance portion) at which blood sample 402 first enters fluid path 420 and travels within fluid path 420.

In some embodiments, fluid path 420 comprises a capillary that is sized and having a cross-sectional shape (e.g., circular, square, etc) suitable for inducing capillary action on a fluid, such as blood. In other embodiments, fluid may be moved through fluid path 420 via other motive sources such as a pressure drop along the fluid path.

Test strip 404 also comprises first chamber 440 and second chamber 442. First chamber 440 is disposed between conduit portion 424 and second chamber 442. A pair of gate electrodes 450 are disposed at a junction of fluid path 420 and first chamber 440. Sensor electrodes 452 are disposed within first chamber 440. Second chamber 442 is disposed at an end of fluid path 420 and comprise sensors 460 disposed within second chamber 442. In some embodiments, second chamber 442 additionally comprises one or more electrode elements 490 on a top wall, side wall, or bottom wall of second chamber 442 for producing a spatially varying electric field within second chamber 442, as will be later described in more detail Several aspects of system 400 affect movement of cells within test strip 404. In one embodiment, three factors affect movement of red blood cells. First, field electrode array 430 comprises a plurality of interleaved electrode elements, each activatable separately as multiple distinct channels so that a spatially varying electric field is applied as a traveling wave across electrode array 430 from first side wall 421 to second side wall 422 of fluid path 420 (or vice versa) to urge cells laterally in a deflection direction (e.g., generally parallel to force arrow $F_T$) from one side of fluid path 420 to the other side.

In one particular embodiment, the electrode array 430 is a four electrode system that is similar to-the electrode arrangement depicted with respect to FIG. 6C. Each of the four interleaved electrode groups varies in polarity with a frequency selected for operation in a negative dielectrophoresis mode. Each of the four electrode groups is controlled independently to provide the traveling wave phenomenon.

Second, with an appropriately sized and shaped fluid path 420, blood sample 402 experiences capillary action that moves blood sample 402 in a first direction (generally parallel to force arrow $F_C$) through fluid path 420 toward second chamber 442. Third, as blood moves through fluid path 420, an electric field applied at gate electrodes 450 effectively forces cells to move in the deflection direction (i.e., generally parallel to force arrow $F_T$) thereby preventing cells (e.g., red blood cells) from entering first chamber 440 and causing them to continue passing down fluid path 420 past first chamber 440 for collection and concentration in second chamber 442. This separating action produces a portion of blood sample 402 that is relatively enriched in cells in second chamber 442 while producing a portion of blood sample 402 that is relatively depleted of cells in first chamber 440.

Sensor electrodes 452 in first chamber 440 are configured for electrochemically measuring glucose within first chamber 440 in the portion of blood sample 402 that has a reduced cell concentration, (i.e. that is relatively depleted of cells). In some embodiments, second chamber 442 comprises sensor(s) 460 configured for electrochemically measuring an analyte glucose within second chamber 442 in the portion of blood sample 402 that is relatively enriched in cells. However, in other embodiments, sensor(s) 460 can be omitted from second chamber 442.

Fluid path 420 generally has a width on the order of about 1-2 millimeters while test strip 404 and fluid path 420 generally has a length on the order of about 10 millimeters. The conductive tracings defining individual electrode elements of electrode array 430 generally are spaced about 10 microns from each other. First chamber 440 can have the geometric configuration shown, or also comprise other shapes and sizes depending on intended use.

Gate electrodes 450 are disposed and arranged to generate a high field region at an opening of first chamber 440 to urge cells away from the opening to first chamber 440 to achieve a blood sample within first chamber 440 that is relatively depleted or devoid of cells, such as red blood cells. Despite the presence of the electric field from gate electrodes 450, capillary action still wicks plasma (blood relatively devoid of red blood cells) into first chamber 440. In some embodiments, gate electrodes 450 are each of a size on the order of 300 microns by 125 microns, and can be formed in a triangular shape having a sharp tip. The tip is oriented into the opening of first chamber 440 and protrudes slightly (e.g., 5 microns) from side wall 421 of test strip 404 for focusing the electric field at the opening of first chamber 440. In addition, a gap between the gate electrode tips (e.g., 100 microns) is generally smaller than the general opening (e.g., 450 microns) into first chamber to further enhance the ability of plasma to enter first chamber 440 while excluding red blood cells.

In addition, in some embodiments, more than two gate electrodes 450 are arranged in an array at the junction of pathway 420 and first chamber 440 to enhance the repelling effect on the cells caused by the pair of gate electrodes 450.

The dimensions and shapes of test strip 404 including fluid path 420, field electrode array 430, gate electrodes 450, and first chamber 440 are intended to be illustrative of the relationship between these components, and not strictly limiting of system 400. For example, the dimensions and shapes of gate electrodes 450 and the opening of first chamber 440 can be modified to optimize a desired balance between the force of induced capillary action that wicks plasma into first chamber 440 and the force of an electric field effect that repels red blood cells from gate electrodes 450. This balancing also takes place for fluid path 420, in which the dimensions and shape of fluid path 420 which dictate the capillary force are balanced against the force imparted by the electric field via electrode array 430.

In some embodiments, the role of first chamber 440 and second chamber 442 are reversed. In particular, gate electrodes 450 are deactivated to permit entry of cells into first chamber 440 and electrode array 430 is operated with a spatially varying electric field that drives toward and into first chamber 440 so that diversion of cells takes place into first chamber 440 instead of into second chamber 442. Gate electrodes 450 are either omitted or simply deactivated. Accordingly, first chamber 440 becomes filled with blood that is relatively enriched in cells and second chamber 442 becomes filled with blood that is relatively depleted of cells. With this arrangement, sensor(s) 460 within second chamber 442 are used to measure an analyte in blood sample 402.

Figure 13:
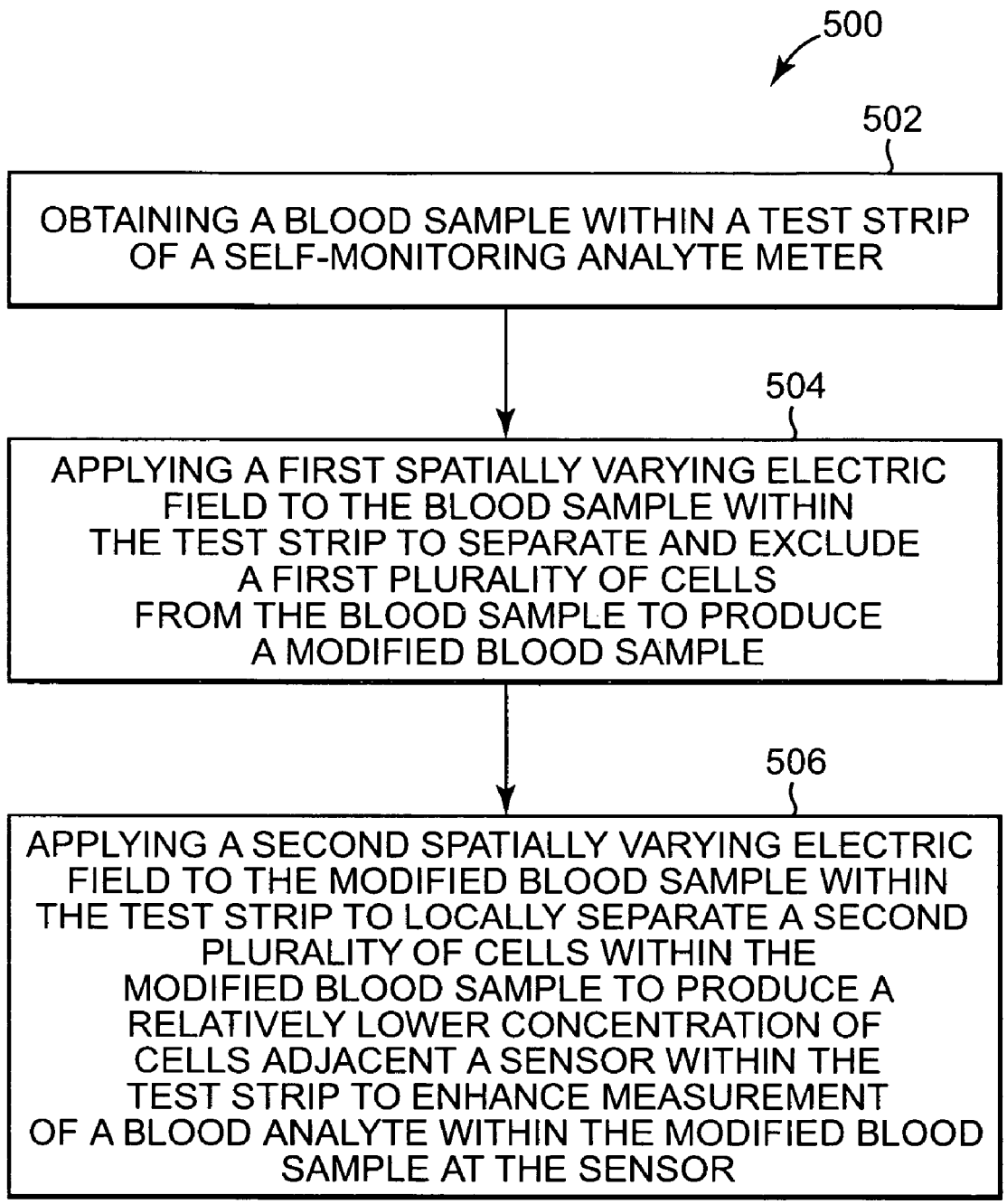
FIG. 13 is a block diagram of a method of testing blood, according to an embodiment of the present invention.

FIG. 13 illustrates a method 500 for measuring a property of a blood sample. As shown in box 502, method 500 comprises obtaining a blood sample within a test strip of a self-monitoring analyte meter. Method 500 further comprises, as shown in box 504, applying a first spatially varying electric field to the blood sample within the test strip to separate and exclude a first plurality of cells from the blood sample to produce a modified blood sample. At this point, the modified blood sample is relatively depleted of cells, which enhances measurement of an analyte (e.g., glucose) within the modified blood sample since fewer cells (e.g., red blood cells) are present to act as interferents in analyte detection. In one embodiment, the modified blood sample is delivered into a test chamber while the cells are diverted elsewhere.

As shown in box 506, another aspect of method 500 comprises applying a second spatially varying electric field to the modified blood sample within the test strip. In one embodiment, this includes applying the field within the test chamber. Since the modified blood sample is already relatively depleted of cells, the application of this second field is used to further decrease cell concentration adjacent a sensor within the test chamber, thereby further minimizing the interference of cells with the sensing of the blood analyte. Accordingly, the second field acts on a second plurality of cells within the modified blood sample to produce a relatively lower concentration of cells relative to a sensor within the test strip to enhance measurement of the analyte (or other blood properties). This activity, shown in box 506, further purifies the modified blood sample in the region of the sensor from cells to further enhance measurement of an analyte, since even fewer cells are present adjacent the sensor. This redistribution of cells prevents interference of cells with diffusion of an analyte (e.g., glucose) in the blood sample for reaction with test enzymes in the test chamber and prevents interference of the cells with migration of analyte-enzyme reaction products to an electrochemical sensor electrode in the test chamber.

Systems and components shown in FIGS. 1-2 are suitable for performing method 500. For example, in some embodiments of method 500, systems and components of FIGS. 1-10 can be used to perform the aspect of method 500 shown in box 504. In some embodiments of method 500, systems and components of FIGS. 11-12 can be used to perform the aspect of method 500 shown in box 506.

Embodiments of the present invention enhance self-monitoring of analytes, and other blood properties, through application of a spatially varying electric field to a blood sample to alter a cell concentration in a portion of the blood sample within a test device for enhancing measurement of an analyte in the test device. Various electrode arrangements are used within the test device, with or without traveling wave dielectrophoresis, to manipulate cells away from the sensor to enhance measuring presence or concentration of blood analytes.

Although specific embodiments have been illustrated and described herein, it will be appreciated by those of ordinary skill in the art that a variety of alternative and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of analyzing blood, comprising:
    delivering a blood sample including cells to a test chamber to directly expose the blood sample to both a sensor and an electrode arrangement within the test chamber;
    applying a spatially varying electric field, via the electrode arrangement, to the blood sample within the test chamber to provide a portion of the blood sample with a depleted cell concentration by electrically redistributing cells within the blood sample away from the sensor; and sensing, via the sensor within the test chamber, a property of the portion of the blood sample.

2. The method of claim 1, wherein the property of the portion of the blood sample is at least one of a presence and a concentration of a blood analyte.

3. The method of claim 1, wherein the depleted cell concentration in a portion of the blood sample corresponds to a plasma rich portion of the blood sample having a reduced red blood cell concentration, and wherein sensing the property of the blood sample comprises measuring the property in the plasma rich portion of the blood sample.

4. The method of claim 1, wherein sensing the property of the blood sample is performed during application of the spatially varying electric field.

5. The method of claim 4, wherein sensing the property of the blood sample is also performed before application of the spatially varying electric field.

6. A blood analyzer, comprising:
a fluid flow path including a test chamber configured to receive a blood sample that includes cells;
a sensor disposed in the test chamber and configured to measure a property of a portion of the blood sample; and
an electrode arrangement disposed in the test chamber and configured to generate a spatially varying electric field in the test chamber to reduce a cell concentration in the portion of the blood sample adjacent to the sensor by electrically distributing cells within the blood sample away from the sensor.

7. The blood analyzer of claim 6, wherein the property comprises at least one of a concentration and a presence of a blood analyte.

8. The blood analyzer of claim 6, further comprising:
a meter including a waveform generator configured for generating a signal that produces the spatially varying electric field and configured for controlling a measurement at the sensor; and
a test strip including the fluid flow path, the sensor, and the electrode arrangement, the test strip being removably insertable into the meter for electrical communication with the meter to receive the signal and to perform the measurement of the property of the blood sample.

9. The blood analyzer of claim 6, wherein the test chamber includes a plurality of walls including a top wall, a bottom wall, and a pair of side walls, wherein the sensor is disposed on one of the plurality of walls that is at least one of opposite from and perpendicular to one of the plurality of walls on which the electrode arrangement is disposed.

10. The blood analyzer of claim 9, wherein the one of the plurality of walls that includes the sensor defines a surface, and wherein the sensor is located below the surface.

11. The blood analyzer of claim 6, wherein the sensor and the electrode arrangement are disposed on a same wall of a plurality of walls of the test chamber.

12. The blood analyzer of claim 11, wherein the sensor and the electrode arrangement define a single unit on a top wall of the test chamber, and the electrode arrangement is configured to impart a traveling wave in the spatially varying electric field to repel cells away from the sensor prior to or during sensing of the property of the blood sample.

13. The blood analyzer of claim 6, wherein the sensor is at least one of an optical sensor mounted external to the fluid flow path and configured to emit light through the fluid flow path to measure the property of the blood sample or an electrochemical sensor mounted within the fluid flow path to measure the property of the blood sample.

14. The blood analyzer of claim 6, wherein the electrode arrangement is at least one of an electrode pair, a spiral electrode array, a linear electrode array, and a nested square electrode array.

15. The blood analyzer of claim 6, wherein the electrode arrangement comprises a plurality of electrode elements in which at least one of the electrode elements includes a hybrid element which defines both the sensor and a field electrode configured to apply the spatially varying electric field in cooperation with the other electrode elements.

16. The blood analyzer of claim 15, further comprising system electronics configured to first apply the spatially varying electric field as a traveling wave to repel cells from both the field electrode and the sensor of the electrode arrangement and to later operate the sensor of the electrode arrangement to measure the property of the blood sample in the relative absence of the cells from the sensor.

17. A method of testing a property of blood in a test strip of a self-monitoring glucose meter, comprising:
obtaining a blood sample within the test strip and external to a test chamber of the test strip,
applying a first spatially varying electric field to the blood sample within the test strip, and external to the test chamber, to separate and exclude a first plurality of red blood cells from the blood sample to produce a modified blood sample;
delivering the modified blood sample into the test chamber; and
applying a second spatially varying electric field to the modified blood sample within the test chamber to produce a relatively lower concentration of red blood cells adjacent a sensor within the test chamber;
measuring a property of the modified blood sample at the sensor within the test chamber.

18. A blood analyzer, comprising:
a fluid flow path for receiving a blood sample;
a sensor disposed in the fluid flow path and configured to measure a property of a portion of the blood sample; and
an electrode arrangement disposed in the fluid flow path and configured to generate a spatially varying electric field in the fluid flow path to reduce a cell concentration in the portion of the blood sample, wherein the electrode arrangement is at least one of an electrode pair, a spiral electrode array, a linear electrode array, or a nested square electrode array, and wherein the electrode arrangement comprises a plurality of electrode elements in which at least one of the electrode elements includes a hybrid element which defines both the sensor and a field electrode configured to apply the spatially varying electric field in cooperation with the other electrode elements.

19. A blood analyzer, comprising:
a fluid flow path including a test chamber and a conduit portion configured to receive a blood sample;
an electrode arrangement disposed in the conduit portion and configured to generate a spatially varying electric field to reduce a cell concentration in a portion of the blood sample within the conduit portion before the blood sample reaches the test chamber; and
a sensor disposed in the test chamber and configured to measure a property of the portion of the blood sample.

20. The blood analyzer of claim 19, wherein the reduced concentration of cells corresponds to a depleted cell concentration in a first portion of the blood sample and an enriched concentration of cells in a second portion of the blood sample.

21. The blood analyzer of claim 20, wherein the fluid flow path includes a collecting chamber, separate from the test chamber, configured to collect the second portion of the blood sample.

22. The blood analyzer of claim 19, wherein the conduit portion is configured to conduct the blood sample in a first direction, and wherein the electrode arrangement is configured to deflect cells in the blood sample in a second direction transverse to the first direction.

23. The blood analyzer of claim 22, wherein the electrode arrangement includes a first portion configured to generate a traveling wave in the spatially varying electric field to deflect cells in the second direction away from the test chamber and a second portion, separate from the first portion, configured to generate a high field region for deflecting cells in the second direction away from the test chamber.

24. The blood analyzer of claim 23, wherein the first portion of the electrode arrangement includes a linear electrode array disposed within the conduit portion of the fluid flow path for generating the traveling wave, and wherein the second portion of the electrode arrangement includes a gate electrode array disposed at a junction of the conduit portion and the chamber and configured to generate the high field region.

* * * * *

UNITED STATES PATENT AND TRADEMARK OFFICE
CERTIFICATE OF CORRECTION

PATENT NO. : 7,384,791 B2 Page 1 of 1
APPLICATION NO. : 10/761535
DATED : June 10, 2008
INVENTOR(S) : David Tyvoll et al.

It is certified that error appears in the above-identified patent and that said Letters Patent is hereby corrected as shown below:

On page 2, item (56), under "U.S. Patent Documents", in column 1, line 16, delete "6,641,708 B1   11/2003    Huang et al." and
insert -- 6,641,708 B1   11/2003    Becker et al. --, therefor.

In column 12, line 40, delete "atest" and insert -- a test --, therefor.

In column 20, line 24, in Claim 17, delete "strip," and insert -- strip; --, therefor.

In column 22, line 12, in Claim 24, insert -- test -- before "chamber".

Signed and Sealed this

Twenty-eighth Day of October, 2008

JON W. DUDAS
*Director of the United States Patent and Trademark Office*